United States Patent [19]
Matsuda et al.

[11] Patent Number: 6,015,830
[45] Date of Patent: Jan. 18, 2000

[54] ANTIBACTERIAL COMPOUNDS FOR *RALSTONIA SOLANACEARUM*

[75] Inventors: Kazuhiko Matsuda, Nara; Hideyoshi Toyoda, Kyoto; Satoshi Harada, Tochigi, all of Japan

[73] Assignee: Kagome Kabushiki Kaisha, Aichi, Japan

[21] Appl. No.: 09/229,207

[22] Filed: Jan. 13, 1999

[30] Foreign Application Priority Data

Feb. 5, 1998 [JP] Japan ................................ 10-041317

[51] Int. Cl.[7] ................ A01N 43/38; C07D 209/04; C07D 209/12; C07D 209/18
[52] U.S. Cl. ............... 514/419; 514/784; 548/491; 548/494; 435/18; 435/196; 435/814; 424/405
[58] Field of Search ................. 424/405; 514/419, 514/784; 435/18, 196, 814; 548/491, 494

[56] References Cited

U.S. PATENT DOCUMENTS 5,496,794   3/1996   Katayama et al. ................ 504/284

*Primary Examiner*—Johann Richter
*Assistant Examiner*—Jane C. Oswecki
*Attorney, Agent, or Firm*—Majestic, Parsons, Siebert & Hsue P.C.

[57] ABSTRACT

Antibacterial compounds for *Ralstonia solanacearum* having substantially (S)-3-(3-indolyl) butanoic acid of a specified structure or its salt as active component can selectively inhibit the growth of *Ralstonia solanacearum* and suppress bacterial wilt dependably even if used at relatively lower concentration.

2 Claims, No Drawings

ANTIBACTERIAL COMPOUNDS FOR *RALSTONIA SOLANACEARUM*

BACKGROUND OF THE INVENTION

This invention relates to antibacterial compounds for *Ralstonia solanacearum*. Bacterial wilt which affects tomatoes, egg plants, green peppers, tobacco plants, Japanese radishes, strawberries and the like is a kind of bacterial disease caused by *Ralstonia solanacearum*. *Ralstonia solanacearum* is known for its very high spreading velocity, and its secondary invasion is very strong. Thus, the bacterial wilt caused thereby can be a source of a severe damage particularly for green-house cultivation and repeated cultivation. This invention relates to antibacterial compounds capable of dependably suppressing such bacterial wilt even if used at a low concentration.

Conventional methods of suppressing bacterial wilt included disinfection by the solar heat, root growth restriction by means of sheets and grafting on resistant cultivar as rootstocks. With these conventional methods, however, manifestation of effects is extremely insufficient. Use of a disinfectant has also been attempted but the use of a disinfectant has bad effects not only on the plants and the soil but also on the workers, besides suppressing bacterial wilt. In view of the above, Japanese Patent Publication Tokkai 7-228502 disclosed the use of synthesized 3-(3-indolyl) butanoic acid and its salts as antibacterial compounds capable of suppressing *Ralstonia solanacearum*. These compounds have the desirable characteristic of being capable of selectively inhibiting the growth of *Ralstonia solanacearum* which is the cause of bacterial wilt and hence suppressing bacterial wilt without having any ill effects on other bodies. Prior art synthesized 3-(3-indolyl) butanoic acid and its salts have the disadvantage, however, in that they must be used at a relatively high concentration in order to selectively inhibit the growth of *Ralstonia solanacearum*.

SUMMARY OF THE INVENTION

It is therefore an object of this invention to provide an antibacterial compound capable of selectively suppressing the growth of *Ralstonia solanacearum* even if used at a relatively low concentration.

This invention is based on the present inventors' discovery that synthesized 3-(3-indolyl) butanoic acid is a racemic body containing both optical isomers (S)-3-(3-indolyl) butanoic acid (which is the S body of 3-(3-indolyl) butanoic acid) and (R)-3-(3-indolyl) butanoic acid (which is the R body of 3-(3-indolyl) butanoic acid) and that it is the former of these two that has a significant chemical effect in selectively inhibiting the growth of *Ralstonia solanacearum* and is hence capable of dependably suppressing bacterial wilt, even if used at a relatively low concentration, without having any ill effects on other bodies.

DETAILED DESCRIPTION OF THE INVENTION

This invention relates to antibacterial compounds for *Ralstonia solanacearum*, of which the active component is substantially (S)-3-(3-indolyl) butanoic acid shown by Equation (1) given below or its salts:

Formula (1)

Synthesized 3-(3-indolyl) butanoic acid is a racemic body which contains as optical isomers both aforementioned (S)-3-(3-indolyl) butanoic acid shown by Formula (1) given above and (R)-3-(3-indolyl) butanoic acid shown by Equation (1) shown by Formula (2) given below:

Formula (2)

As will be shown below more in detail, (S)-3-(3-indolyl) butanoic acid given by Formula (1) above can be obtained through the following three processes: (1) First Process wherein a condensation product of meldrum's acid and acetoaldehyde is caused to undergo an addition reaction with indole to obtain a reaction product; (2) Second Process wherein the reaction product obtained in the First Process is dissolved in a mixed liquid of pyridine and alcohol, copper is added thereto and a decarboxylation reaction is caused by heating under reflux to obtain esters of racemic body of 3-(3-indolyl) butanoic acid; and (3) Third Process wherein the esters obtained in the Second Process are subjected to an enzymic process by using lipase which is capable of selectively dissociating by hydrolysis only esters of (S)-3-(3-indolyl) butanoic acid contained in the aforementioned esters obtained in the Second Process to thereby obtain (S)-3-(3-indolyl) butanoic acid.

Examples of salt of (S)-3-(3-indolyl) butanoic acid shown by Equation (1) include those of an alkali metal such as potassium and sodium, those of an alkali earth metal such as calcium and magnesium and ammonium salt.

As will be described below in more detail, (S)-3-(3-indolyl) butanoic acid shown by Equation (1) and its salts are more effective in selectively preventing the growth of *Ralstonia solanacearum* than (R)-3-(3-indolyl) butanoic acid or its salts, and also more effective than the racemic body of 3-(3-indolyl) butanoic acid which is a mixture of these two, as well as its salts, and hence can dependably suppress bacterial wilt even at a low concentration without rendering any ill effects to other bodies.

Embodiments of this invention may be considered to include the following:
 (1) antibacterial compounds for *Ralstonia solanacearum* having (S)-3-(3-indolyl) butanoic acid shown by Equation (1) as active component;
 (2) antibacterial compounds for *Ralstonia solanacearum* having sodium salt of (s)-3-(3-indolyl) butanoic acid shown by Equation (1) as active component; and
 (3) antibacterial compounds for *Ralstonia solanacearum* having ammonium salt of (S)-3-(3-indolyl) butanoic acid shown by Equation (1) as active component.

The invention will be explained next by way of the results of experiments carried out.

Experiment Part 1

Indole 3 g and meldrum's acid 4.43 g were dissolved in 30 ml of acetonitrile, and 3 ml each of acetaldehyde refined immediately before by distillation was added both at the beginning time of the reaction and 2 hours later to cause a reaction at 30° C. for 6 hours with stirring. After the reaction liquid was condensed at a reduced pressure, it was dissolved in a mixed solvent of pyridine 30 ml and ethanol 3 ml, and copper particles 150 mg were added for a reaction by heating under reflux for 6 hours. After the reaction liquid was filtered and the filtered liquid was made acidic (according to its pH) by adding 2N hydrochloric acid, ether was used for extraction. The extracted liquid was washed with water and after it was dried with anhydrous magnesium sulfate, the solvent was distilled away under a reduced pressure. The residue was refined by silica gel column chromatography (gel: Wakogel C-200 (trade name of product by Wako Pure Chemical Industries, Ltd. which is a silica sol for column chromatograph); solvent : hexane/ethyl acetate=5/1) to obtain 2.25 g of ethyl ester of racemic body of 3-(3-indolyl) butanoic acid. A 1/1 mixture 20 ml of ethanol and 10% aqueous solution of potassium hydroxide was added to this ethyl ester of racemic body of 3-(3-indolyl) butanoic acid 2.25 g, and it was dried and hardened by means of an evaporator after 6 hours of reflux. Water was added to this hardened dry substance, and it was washed with ether. After active charcoal was added for decolorization with heat, it was filtered to remove the active charcoal. Crystal 1.85 g of racemic body of 3-(3-indolyl) butanoic acid was obtained by adding 2N hydrochloric acid to the decolored liquid to make the solution acidic.

Experiment Part 2

Ethyl ester 53.6 mg of racemic body of 3-(3-indolyl) butanoic acid, produced during the course of Experiment Part 1 was dissolved in 0.1M acetic acid buffer (pH=5) containing t-butanol by 10%, and Lipase AK (trade name of product by Amano Pharmaceutical Co., Ltd. which is a fat-decomposing enzyme separated from a metabolism product of Pseudomonas fluorescens which hydrolyses only the S body of optical isomers). The reaction liquid was filtered with celite and, after the filtered liquid was made acidic (according to its pH) by adding 1N hydrochloric acid, it was extracted by using ethyl acetate. After the extracted liquid was dried with anhydrous sodium sulfate, the solvent was distilled away under a reduced pressure. The residue was analyzed through a silica gel column (gel : Wakogel). First, ethyl ester 13.4 mg of (R)-3-(3-indolyl) butanoic acid not decomposed by Lipase AK was eluted out by using a mixture of dichloromethane/ethyl acetate=9/1 as solvent. Next, (S)-3-(3-indolyl) butanoic acid 13.1 mg was obtained by elution by using a mixture of dichloromethane/ethyl acetate=1/1. The optical purity of (S)-3-(3-indolyl) butanoic acid by a high performance liquid chromatography (HPLC) method was 99%.

Experiment Part 3

The ethyl ester 13 mg of (R)-3-(3-indolyl) butanoic acid obtained in Experiment Part 2 above was dissolved in 0.1M phosphoric acid buffer (pH=7.3) containing t-butanol by 10%. Porcine liver esterase (trade name of product by Sigma-Aldrich Co. which is an ester-decomposing enzyme extracted from the liver of a pig) 62 mg was added to this solution for a reaction at 30° C. for 24 hours with stirring. The reaction liquid was filtered and after 1N hydrochloric acid was added to the filtered liquid to make it acidic (according to its pH), it was extracted by using ethyl acetate. The extracted liquid was washed with water and after it was dried by using anhydrous sodium sulfate, the solvent was distilled away under a reduced pressure. The residue was refined by silica gel column chromatography (gel: Wakogel C-200; solvent dichloromethane/ethyl acetate=1/1) to obtain 7 mg of (R)-3-(3-indolyl) butanoic acid. Its optical purity by the HPLC method was 99%.

Experiment Part 4

By the minimum inhibitory concentration (MIC) method which will be described in detail below, antibacterial activities against *Ralstonia solanacearum* race 1 of the racemic body, the S body and the R body of 3-(3-indolyl) butanoic acid obtained in Experiment Parts 1, 2 and 3 described above were measured. The results are shown in Table 1 below.

According to this MIC method, the racemic body, the S body and the R body of 3-(3-indolyl) butanoic acid obtained in Experiment Parts 1, 2 and 3 were each dissolved in 4% methyl alcohol and these solutions were each mixed with an equal amount of a double-strength PCG liquid medium (bactopeptone 10 g+casamino acid 1 g+glucose 10 g per liter) such that the concentrations (in $\mu$g/ml) of the racemic body, the S body and the R body would be as given in Table 1. The liquid medium thus prepared was filtered through a membrane of pore size 0.22 $\mu$m to reduce the bacteria count to provide a test medium. Separately, *Ralstonia solanacearum* race 1 bacteria were preliminarily cultivated by using a PCG liquid medium and after they were collected, a bacterial suspension of 5×10$^5$ cell/ml was obtained in physiological brine. This bacterial suspension 60 $\mu$l was inoculated to 3 ml of the aforementioned test medium and stirred for cultivation at 30° C. for 24 hours. The growth of *Ralstonia solanacearum* race 1 bacteria was measured by using as indicator the turbidity of this culture liquid at 600 nm. Since the turbidity of the culture liquid would be the same as that of an uninoculated culture liquid if the growth of *Ralstonia solanacearum* race 1 bacteria were completely inhibited by the racemic, S or R body, the concentration of the racemic, S or R body at such a time was defined as the MIC.

TABLE 1

| Concentration ($\mu$g/ml) | | 0 | 0.5 | 1.0 | 2.5 | 5 | 10 | 25 |
|---|---|---|---|---|---|---|---|---|
| Growth | Racemic body | + | + | + | − | − | − | − |
| | S body | + | + | − | − | − | − | − |
| | R body | + | + | + | + | + | − | − |

In TABLE 1:
+: Growth observed
−: Growth inhibited

Table 1 shows that the MIC of 3-(3-indolyl) butanoic acid against *Ralstonia solanacearum* race 1 is about 10 $\mu$g/ml in the case of R body and about 2.5 $\mu$g/ml in the case of racemic body but that it is about only 1.0 $\mu$g/ml in the case of S body. This means that the use of (S)-3-(3-indolyl) butanoic acid or its salt as antibacterial compound is far more effective in inhibiting the growth of *Ralstonia solanacearum* and hence in dependably and selectively suppressing bacterial wilt even if used at a relatively lower concentration without causing any ill effects on other bodies.

What is claimed is:
1. An antibacterial composition for *Ralstonia solanacearum* comprising as an active component of said com- position (S)-3-(3-indolyl) butanoic acid shown by Formula 1 given below or a salt thereof:

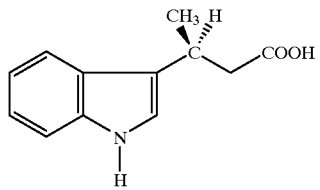

Formula 1 and an antibacterially acceptable carrier or dilvent.

2. A method of obtaining the (S)-3-(3-indolyl) butamoic acid of the antibacterial composition of claim 1, said method comprising the steps of:

reacting a condensation product of meldrum's acid and acetoaldehyde with indole to obtain a first reaction product by an addition reaction;

dissolving said first reaction product in a mixed liquid of pyridine and alcohol, adding copper thereto and causing a decarboxylation reaction by heating under reflux to obtain esters of a racemic body of 3-(3-indolyl) butanoic acid, and subjecting said esters of the racemic body of 3-(3-indolyl) butanoic acid to an enzymic process by using lipase which is capable of selectively dissociating by hydrolysis only esters of (S)-3-(3-indolyl) butanoic acid contained in said esters of racemic body of 3-(3-indolyl) butanoic acid to thereby obtain (S)-3-(3-indolyl) butanoic acid shown by Formula 1.

* * * * *